United States Patent [19]
Dietrich et al.

[11] 3,943,158
[45] Mar. 9, 1976

[54] UREA DIISOCYANATE COMPOSITIONS

[75] Inventors: Werner Dietrich, Cologne; Kuno Wagner, Leverkusen, both of Germany; Willi Eifler, New Martinsville, W. Va.

[73] Assignee: Bayer Aktiengesellschaft, Leverkusen, Germany

[22] Filed: Sept. 6, 1973

[21] Appl. No.: 394,710

Related U.S. Application Data

[63] Continuation-in-part of Ser. No. 155,606, June 22, 1971, abandoned.

[30] Foreign Application Priority Data

July 1, 1970   Germany............................ 2032547

[52] U.S. Cl. 260/453 A; 260/2.5 AT; 260/77.5 AT; 260/453 AL; 260/453 AR; 260/453 P
[51] Int. Cl.² ............ C07C 119/042; C07C 119/045; C07C 119/048
[58] Field of Search ... 260/453 AB, 453 P, 453 AR, 260/453 AL, 453 A

[56] References Cited
UNITED STATES PATENTS

| 3,124,605 | 3/1964 | Wagner............................... 260/453 |
| 3,284,479 | 11/1966 | Windemuth et al. ................ 260/453 |
| 3,441,588 | 4/1969 | Wagner et al. ..................... 260/453 |

*Primary Examiner*—Lewis Gotts
*Assistant Examiner*—Dolph H. Torrence
*Attorney, Agent, or Firm*—Joseph C. Gil; Gene Harsh

[57] ABSTRACT

The present invention relates to stable solutions of urea diisocyanates in diisocyanates which are free from urea groups which solutions are prepared by a process which comprises reacting in the absence of a solvent at a temperature from about −20°C to about 80°C an organic diisocyanate with a bis-secondary diamine such that the NCO/NH-ratio is from 2.5 : 1 to 20 : 1. The solutions of the invention are well-suited for use as isocyanate component for the preparation of polyurethane resins by the isocyanate polyaddition process.

1 Claim, No Drawings

UREA DIISOCYANATE COMPOSITIONS

This application is a continuation-in-part of co-pending U.S. Pat. application Ser. No. 155,606 filed on June 22, 1971 now abandoned.

Cellular and non-cellular synthetic resins containing urethane groups, of the type obtained by reacting polyols with polyisocyanates, are widely used, e.g. in the field of insulation, for the production of structural elements or for upholstery purposes.

It is known that the physical properties of many polyurethane resins can be advantageously affected by the incorporation of urea groups. In the case of foam resins, these urea groups are, in most cases, produced by the addition of water to the foam formulation. The resulting isocyanate hydrolysis causes 1 mol of gaseous carbon dioxide to be split off per mol of water. This method may be disadvantageous in cases where the polyurethane foam resin obtained is to be used for insulating purposes. A hard foam resin which has been blown up with carbon dioxide has only 50 to 70% of the heat insulating effect of foam resins whose cells are filled with gaseous organic halogen compounds such as monofluorotrichlorourethane. The method usually adopted for non-cellular polyurethane resins is that a certain amount of diamines or polyamines is added to the polyol and the urethane polyaddition reaction is coupled with the reaction of amines with isocyanates to produce ureas, or alternatively an NCO prepolymer of diols and diisocyanates is crosslinked with amines. The amount of polyamine in the formulation is limited by the natural activity of amines towards isocyanates.

Both methods could be circumvented by using for the isocyanate, polyaddition isocyanates, which already contain urea-groups. This method has hitherto been unsuccessful because both ureas prepared from water and diisocyanates and those prepared from the conventional primary diamines and polyamines with isocyanates are insoluble in excess monomeric isocyanate and working up suspensions by the usual methods of polyurethane technology gives rise to difficulties, (when water is reacted with 2,4-toluylene diisocyanate by the method described in U.S. Pat. No. 2,757,185, a urea adduct is obtained which immediately precipitates from monomeric diisocyanate at room temperature).

It has now surprisingly been found that adducts of diisocyanates and diamines which are soluble in excess monomers can be obtained by reacting isocyanates with special amines. The special amines used according to the invention are aromatic, araliphatic, aliphatic and cycloaliphatic diamines which have only secondary amino groups.

The present invention, therefore, relates to a stable homogeneous solution of urea diisocyanates of the formula

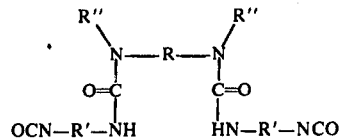

in diisocyanates of the formula OCN—R'—NCO prepared by a process which comprises reacting in the absense of a solvent at a temperature from about −20°C to about 80°C an organic diisocyanate of the formula OCN—R'—NCO with a diamine of the formula R"—NH—R—NH—R" such that the NCO/NH-ratio is from 2,5 : 1 to 20 : 1.

In these formulae R stands for an aliphatic, cycloaliphatic, aromatic or araliphatic hydrocarbon radical having up to 25 carbon atoms, R' stands for an aliphatic, cycloaliphatic, aromatic or araliphatic hydrocarbon radical having up to 13 carbon atoms and R" stands for an alkyl radical having 1 to 4 carbon atoms.

To prepare the solutions of urea diisocyanates in diisocyanates free from urea groups the amines used as starting materials are used in a proportion which corresponds to an NCO/NH ratio of 2.5 : 1 to 20 : 1. When preparing the solutions according to the invention it is advantageous, especially since no inert solvents are present, to add the amines to the isocyanate at a temperature which is above the melting point of the amine used. In addition, care should be taken to ensure that the upper temperature limit of 80°C is not exceeded. This means that the process for preparing the solutions according to the invention is carried out at −20°C to +80°C and preferably at temperatures in the region of +20°C to +70°C.

As a general rule, the process yields polyisocyanates which contain urea groups, in the form of solutions in the polyisocyanate free from urea groups which was used as starting material. In cases where diisocyanates which have a high vapour pressure are to be converted into physiologically harmless urea adducts the excess monomeric diisocyanate may also be removed by distillation on a thin layer evaporator.

The secondary diamines used in the process according to the invention are diamines of the formula R'λ'—NH—R—NH—R" wherein R stands for an aliphatic, cycloaliphatic, aromatic or araliphatic hydrocarbon radical having up to 25 carbon atoms and R" stands for an alkyl radical having 1 to 4 carbon atoms. The preferred diamines are those of above formula in which R stands for an aliphatic hydrocarbon radical having 2 to 6 carbon atoms, a cycloaliphatic hydrocarbon radical having 6 to 13 carbon atoms, an aromatic hydrocarbon radical having 6 to 13 carbon atoms or an araliphatic hydrocarbon radical having 8 carbon atoms. Typical examples for suitable diamines are the following: N,N'-dimethyl-2,4-toluylenediamine, N,N'-dimethyl-2,6-toluylenediamine, N,N'-diethyl-2,4-toluylene diamine, N,N'-dipropyl-2,4-toluylenediamine, N,N'-diisopropyl-2,4-toluylenediamine, N,N'-diisopropyl-2,6-toluylenediamine, N,N'-dibutyl-2,4-toluylenediamine, N,N'-dimethyl-4,4'-diaminodiphenylmethane, N,N'-diethyl-4,4'-diaminodiphenylmethane, N,N'-dipropyl-4,4'-diaminodiphenylmethane, N,N'-diisopropyl-4,4'-diaminodiphenylmethane, N,N'-dimethyl-p-phenylenediamine, N,N'-diisopropyl-p-phenylenediamine, N,N'-diisopropyl-2,6-diamino-3,5-diethyltoluene, N,N'-diisopropyl-2,4-diamino-3,5-diethyl-toluene, N,N'-diisopropyl-4,4'-diamino-diphenyl-dimethylmethane, N,N'-diisopropyl-4,4'-diaminodiphenyl-dicyclohexylmethane, N,N'-dimethylethylenediamine, N,N'-diisopropylethylenediamine, N,N'-diisopropylpropylenediamine, N,N'-diisopropyl-1,4-diaminobutane, N,N'-diisopropylhexamethylenediamine, N,N'-diisobutylhexamethylene diamine, N,N'-diisopropyldiaminomethyl-cyclobutane, N,N'-diisopropyltrimethylhexamethtlendiamine, N,N'-diisopropyl-4,4-diaminodicyclohexylmethane, N,N'-diisopropyl-m-xylylenediamine, N,N'-diisopropyl-p-xylylenediamine, N,N'-diisopropyl-3,3,5-trimethyl-5-aminomethyl-cyclohexylamine.

The polyisocyanates used are those of the general formula OCN—R'—NCO wherein R' stands for an aliphatic, cycloaliphatic, aromatic or araliphatic hydrocarbon radical having up to 13 carbon atoms. The preferred diisocyanates are those of above formula in which R stands for an aliphatic hydrocarbon radical having 4–6 carbon atoms, a cycloaliphatic hydrocarbon radical having 6–13 carbon atoms, an aromatic hydrocarbon radical having 6–13 carbon atoms or an araliphatic hydrocarbon radical having 8 carbon atoms.

Typical examples for suitable diisocyanates are: tetramethylenediisocyanate, hexamethylenediisocyanate, m-xylylenediisocyanate, p-xylylenediisocyanate, 4,4'-dimethyl-1,3-xylylene diisocyanate, cyclohexane-1,4-diisocyanate, dicyclohexylmethane-4,4'-diisocyanate, 3,3,5-trimethyl-5-isocyanatomethyl-cyclohexylisocyanate (= isophorone diisocyanate), m-phenylenediisocyanate, p-phenylenediisocyanate, 1-alkylbenzene-2,4- and -2,6-diisocyanates such as toluylene-2,4-and -2,6-diisocyanate, 1-benzylbenzene-2,6-diisocyanate, 2,6-diethylbenzene-1,4-diisocyanate, diphenylmethane-4,4'-diisocyanate and naphthylene-1,5-diisocyanate. The most preferred diisocyanates are hexamethylene diisocyanate, 2,4- and 2,6-toluylene diisocyanate and 4,4'-diisocyanatodiphenylmethane.

The solutions according to the invention are, as already mentioned above, valuable starting materials for the production both of foamed and of unfoamed polyurethane resins.

Especially suitable reactants for the polyisocyanate solutions are compounds which contain hydroxyl and/or carboxyl groups, especially for the production of foam resins. The polyhydroxyl compounds used generally have molecular weights of 100 to 5000, e.g. polyesters, polyethers, polythioethers, polyacetals, polycarbonates and polyester amides, all containing several hydroxyl groups, of the type already known for the production of homogeneous as well as cellular polyurethanes.

Suitable hydroxyl polyesters are, for example, the wide variety of reaction products of polyhydric alcohols with polybasic carboxylic acids used industrially. Instead of free carboxylic acids, however, there may also be used the corresponding polycarboxylic acid anhydrides or polycarboxylic acid esters. The following are mentioned as individual examples of these compounds: Succinic acid, adipic acid, sebacic acid, phthalic acid, isophthalic acid, phthalic acid anhydride, maleic acid, maleic acid anhydride, monomeric, dimeric and trimeric fatty acids, dimethyl terephthalate, etc. The following are examples of suitable polyol components: Ethylene glycol, propylene glycol-(1,3), butylene glycol-(1,4) and -(2,3), glycerol, trimethylolpropane, hexanetriol-(1,2,6), butanetriol-(1,2,4)-trimethylolethane, pentaerythritol, mannitol and sorbitol, methylglycoside, polyethyleneglycols, polypropylene glycols and polybutylene glycols. Polyesters which have terminal carboxyl groups are also suitable for the reaction according to the invention with the polyisocyanates.

The hydroxyl polyethers suitable are also of known type and prepared e.g. by the polymerisation of epoxides such as ethylene oxide, propylene oxide, butylene oxide, styrene oxide or epichlorohydrin, optionally with starting components which have reactive hydrogen atoms such as alcohols or amines, e.g. glycerol, trimethylolpropane, pentaerythritol, sorbitol, ammonia, ethanolamine, ethylenediamine, ethyleneglycol, propanediol, butanediol, resorcinol, hydrofuran, 2,2-bis-(p-hydroxyphenyl)-propane, bis-(p-hydroxyphenyl)methane, bisN,N-alkyl-toluylenediamine and bis-N,N'-alkyl-diamino-diphenylmethane.

Sucrose polyethers are also suitable. Especially to be mentioned in this connection is the capacity of urea modified polyisocyanates to be foamed up with hard foam polyethers which have a high ethylene oxide content and high OH number. Polyethers of this type have the technological advantages, when used, of low viscosity and high activity due to the presence of primary OH groups. Polyethers of this type are difficult to foam up with unmodified organic polyisocyanates such as toluylenediisocyanate or 4,4'-diisocyanatodiphenylmethane owing to the low miscibility. When the urea polyisocyanates used according to the invention are combined with the ethylene oxide polyethers described above, high grade polyurethane foam resins are obtained which combine high compression strength and thermal stability with excellent toughness.

Representatives of the polyhydroxyl compounds are described e.g. in Saunders—Frisch, *Polyurethanes, Chemistry and Technology* Volumes I and II, Interscience publishers 1962 and 1964 (page 32 et seq. Volume I and page 5 and page 198 et seq, Volume II) and in *Kunststoff—Handbuch*, Volume VII, Vieweg-Hochtlen, publishers Carl-Hanser, Munich 966, e.g. on pages 45 to 71. Epoxy resins, hydrogenation products of ethylene, olefine and carbon dioxide copolymers, phenol formaldehyde resins which have been reacted with alkylene oxides and urea formaldehyde resins which have been reacted with alkylene oxides may also be used. A certain amount of low molecular weight polyhydroxyl compounds, e.g. of the type already mentioned above and/or chain lengthening agents such as glycols, diamines or water, aldimines and ketimines may also be included.

Foam production itself is carried out by known methods at room temperature or elevated temperatures imply by mixing the polyisocyanate combinations with the compounds which carry hydroxyl and/or carboxyl groups, optionally with the addition of water, catalysts emulsifiers and other additives such as flame retarding substances and blowing agents. Mechanical devices are advantageously used for this purpose, e.g. those described in French Pat. 1,074,713.

Numerous flame retarding substances are known in the art and generally contain phosphorus and halogens. Compounds of antimony, bismuth or boron may also be used. A survey of known and advantageous flame retarding agents may be found in the chapter "Flammhemmende Substanzen", pages 110–111 of *Kunststoff—Handbuch*, Volume VII, Polyurethane, by Vieweg-Hochtlen, Carl-Hanser-Verlag, Munich 1966. The flame-retarding substances are generally added in quantities of 1–20% by weight, preferably 1–15% by weight, based on the quantity of polyisocyanate combinations used.

Suitable blowing agents are e.g. alkanes, haloalkanes or low boiling solvents generally, e.g. methylene chloride, monofluorotrichloromethane, difluorodichloromethane, acetone, methylformamide, etc. Compounds which split off gas at elevated temperatures, such as azo compounds or diurethanes of bis-semiacetals and 2 mols of formaldehyde and 1 mol of ethylene glycol also constitute suitable blowing agents.

Suitable activators include e.g. tertiary amines such as triethylamine, dimethylbenzylamine, tetramethylethylene diamine, N-alkylmorpholines, endoethylenepiperazine, urotropine, hexahydrotriazines such as trimethylhexahydrotriazine, 2,4,6-dimethylaminomethylphenol and organic metal salts such as tin(II) acylates, e.g. tin(II) salts of 2-ethylcaproic acid, dialkyltin (IV) acylates such as dibutyltin dilaurate or acetyl acetonates of heavy metals e.g. of iron.

Suitable emulsifiers are e.g. oxyethylated phenols, higher sulphonic acids, sulphonated castor oil, oxyethylated castor oil, sulphonatted ricinoleic acid and ammonium salts of oleic acid. Suitable foam stabilisers are e.g. those based on polysiloxane-polyalkylene glycol copolymers or basic silicone oils. Other suitable emulsifiers, catalysts and additives are mentioned e.g. in *Polyurethanes, Chemistry and Technology* Volumes I and II, Saunders—Frisch, Interscience Publishers, 1962 and 1964.

The solutions which contain urea diisocyanates should generally be used in quantities which are equivalent to the sum of reactive hydrogen atoms present, although an excess or subequivalent amount may in some cases be used if desired. In the case of the production of foam resins, if water is used as blowing agent then an excess of polyisocyanates corresponding to the amount of water will be used. Excess amounts of isocyanates may also be built into the foam resin in the form of isocyanurate groups, uretdione groups and/or carbodiimide groups in the course of the foaming process by the addition of trivalent or pentavalent phosphorous compounds such as phospholidines, phospholine oxides, tertiary esters, amides or ester amides.

The foam resins obtained from urea diisocyanates are widely used, e.g. in the building industry as building panels, sandwich elements, ceiling panels or parapet panels, for heat insulation in refrigerators, cold storage houses, refrigerator trucks and refrigeration containers, in road and railway construction, for the technical insulation of pipes, for the insulation of fuel depots, in shipbuilding, as air filters and carbon dioxide filters in internal combustion engines and as shock absorbing packaging material. The foamable products of the process may be hard, semi-hard or flexible and may, therefore, be used as cushion material. The process according to the invention may also be used for the production of semihard or hard polyurethane resins which are foamed in the mould and have a compact surface and cellular core, surprisingly smooth, homogeneous and heat resistant outer zones and cellular cores being obtained.

Diurea diisocyanates obtained from the above mentioned aliphatic, cycloaliphatic or araliphatic diamines and light-fast diisocyanates such as tetramethylene diisocyanate, hexamethylenediisocyanate, m- and p-xylylene diisocyanate and isophorone diisocyanate may be used for the production of lacquer coatings, laminates and elastomers which have maximum light fastness.

EXAMPLES

Example 1

672 Parts by weight of hexamethylenediisocyanate are heated to 60°C. 272 Parts by weight of N,N'-diisopropyl-m-xylylenediamine are introduced dropwise into the polymer in the course of 3 hours with vigorous stirring. The reaction mixture is cooled and a crude, but homogeneous and clear solution which contains about 64% by weight of a diurea diisocyanate which has the following formula:

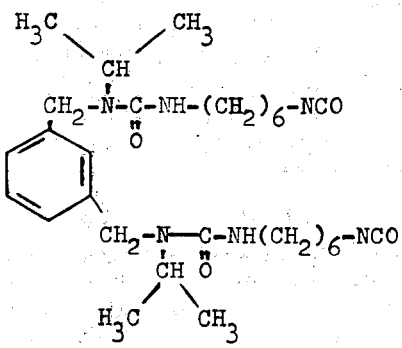

is obtained. NCO content of the solution: 23.6%. The solution is freed from monomeric hexamethylene diisocyanate in a thin layer evaporator at 0.02 mm Hg and 80°C. A viscous, lightfast diurea diisocyanate which has an NCO value of 14.5% is obtained.

Whereas the above mentioned crude solution may be used for preparing lightfast cellular synthetic resins, the diisocyanate which has been purified in the thin layer evaporator may be used for producing lightfast lacquer coatings as described below.

50 Parts by weight of a polyester of 3 mols of phthalic acid and 4 mols of trimethylolpropane having a hydroxyl group content of 10.1% are made up into a paste with 50 parts by weight of a solvent mixture of equal parts of toluene, ethyl acetate butylacetate and glycol monomethylether acetate and 53 parts by weight of titanium dioxide (rutile type). A further 90 parts by weight of the solvent mixture and 1.1 parts by weight of a polyvinylmethylether are added to this paste as levelling agent. A solution of 86 parts by weight of the diurea diisocyanate which has been purified in the thin layer evaporator is now added to the mixture in the form of a solution in 50 parts by weight of xylene/ethyl glycol acetate (1:1). After application of this lacquer mixture on wood, metal or glass, lightfast lacquers are obtained which dry in 8 to 12 hours. By the end of 3 days, the films have become hardened and resistant to solvents and have excellent gloss retention.

Example 2

672 Parts by weight of hexamethylenediisocyanate are reacted with 200 parts by weight of N,N'-diisopropylhexamethylenediamine under the conditions described in Example 1. A crude but homogeneous and clear solution which contains about 61% by weight of a diurea diisocyanate of the following formula:

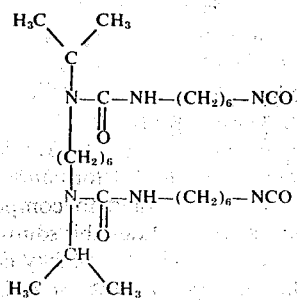

is obtained. NCO content of the solutions: 27.7%. The solution is freed from monomer by the method described in Example 1. The NCO content of the viscous polyisocyanate is 12.2%.

A 50% solution of this polyisocyanate in ethyl acetate containing 0.02% by weight of tin-II-acetate is applied to glass. The one-component lacquer mixture cross links in the course of 24 hours to a lightfast clear lacquer of high elasticity good chemical resistance and excellent gloss retention.

Example 3 a. 1008 Parts by weight of hexamethylenediisocyanate are reacted with 240 parts by weight of N,N'-diisopropyl-3,3,5-trimethyl-5-aminomethyl-cyclohexylamine under the conditions described in Example 1. A crude but homogeneous and clear solution containing approximately 46% by weight of a diurea diisocyanate which has the following formula

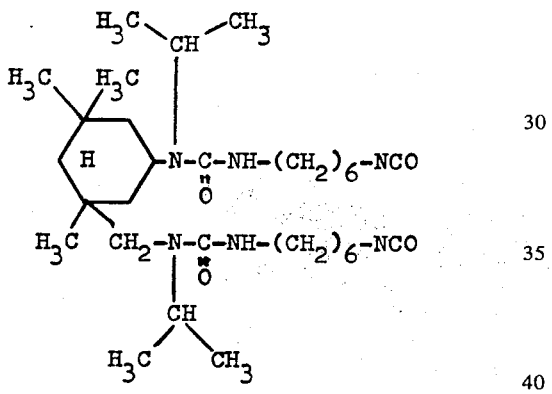

is obtained. Crude solution A: 32.9% NCO.

When the quantity of hexamethylene diisocyanate used in this example is replaced by 6 mols of isophorone diisocyanate or m-. and p-xylylenediisocyanate, completely clear crude solutions which are very stable in storage are again obtained, these solutions have no tendency to separate out insoluble polyurea even when left to stand for several months.

b. This example illustrates the use of diurea diisocyanate prepared in Example 3 for the production of rubbery elastic coatings.

200 Parts by weight of a polyester of adipic acid and ethylene glycol of OH number 56 are dehydrated at 120°C and 14 mm Hg and then mixed at 70°C with 200 parts by weight of methyl ethyl ketone and 25.6 parts by weight of the crude solution A of Example 3 (NCO = 32.9%). The mixture is heated for 2 hours at 60°C, and after a high increase in the viscosity of the solution 100 parts by weight of dimethylformamide are added. Polyaddition is then continued to completion in the course of 3 hours at 70°C. When this solution is painted on a textile fabric or wood, a non-tacky coating which has high lightfastness and high elasticity is obtained.

Example 4 a. 497.11 g of N,N'-dimethyl-4,4'-diamino-diphenylmethane are added dropwise to 1928 g of a mixture of 80% of 2,4- and 20% of 2,6-toluylene diisocyanate with stirring at 55°C. A stable homogeneous and clear liquid isocyanate mixture which contains urea groups and has an NCO content of 29.2% and a viscosity of 980 cP/25°C is obtained.

b. A mixture of 100 g of a propylene oxide polyether of OH number 470 which has been started on sorbitol, 1.5 g of endoethylenepiperazine, 1 g of silicone stabiliser (SF 1109 of General Electric) and 40 g of monofluorotrichloromethane is vigorously stirred up with 120 g of the isocyanate described under 4a). A hard PUR foam which has the following mechanical properties is obtained:

| | |
|---|---|
| Unit weight: | 27 kg/m$^3$ |
| Compression strength: | 2.0 kg wt/cm$^2$ |
| Resistance to bending at elevated temperature | 130°C. | c. A mixture of 100 g of an ethylene oxide polyether of OH number 510 which was started on trimethylolpropane and sucrose (ratio approximately 1:1), 1 g of silicon stabiliser (SF 1109 of General Electric), 0.3 g of endoethylene piperazine and 40 g of monofluorotrichloromethane is intensively stirred together with 130 g of the polyisocyanate described under 4a). A hard PUR foam which has the following mechanical properties is obtained:

| | |
|---|---|
| Unit weight: | 28 kg/m$^3$ |
| Compression strength: | 2.1 kg wt/cm$^2$ |
| Resistance to bending at elevated temperature: | 136°C. |

Example 5 a. 94 g of N,N'-diethyl-diamino-diphenylmethane are added dropwise at room temperature to 1918 g of crude 4,4'-diisocyanatodiphenylmethane. A homogeneous clear liquid polyisocyanate mixture which contains urea groups and has an NCO content of 27 % and a viscosity of 1923 cP (at 25°C) is obtained.

b. A mixture of 100 g of a propylene oxide polyether of OH number 370 which was started on sucrose, 1 g of endoethylenepiperazine, 0.5 g of water, 1 g of silicon stabiliser (SF 1109 of General Electric) and 40 g of monofluorotrichloromethane is intensively stirred together with 117 g of the polyisocyanate prepared under 5a). A hard PUR foam which has the following mechanical properties is obtained:

| | |
|---|---|
| Unit weight: | 33 kg/m$^3$ |
| Compression strength: | 2.7 kg wt/cm$^2$ |
| Resistance to bending at elevated temperature | 140°C. |

Example 6

268 G of a mixture of 80% of 2,4- and 20% of 2,6-toluylene diisocyanate are reacted with 65:25 g of N,N'-diethyl-4,4'-diamino-2,2'-dimethyl-diphenylmethane as described under Example 4a). A homogeneous clear liquid mixture containing urea diisocyanate is obtained which has an NCO content of 32.2 % and a viscosity of 66.3 cP (at 25°C).

Example 7

282 G of 2,4-toluylene diisocyanate are reacted with 65.2 g of N,N'-dimethyl-p,p'-diamino-diphenyl-2,2-propane as in Example 4a). A homogeneous clear liquid mixture containing ureas diisocyanate is obtained which has a NCO content of 32.8 % and a viscosity of 52.6 cP (at 25°C).

What is claimed is:

1. A stable homogeneous clear solution of an urea diisocyanate of the general formula

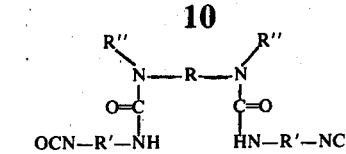

in a diisocyanate of the formula OCN—R'—NCO wherein R is an aliphatic, cycloaliphatic, aromatic or araliphatic hydrocarbon radical having up to 25 carbon atoms, R' is an aliphatic, cycloaliphatic, aromatic or araliphatic hydrocarbon radical having up to 13 carbon atoms and R'' is an aliphatic hydrocarbon radical having 1 to 4 carbon atoms prepared by a process which comprises reacting in the absense of a solvent at a temperature from about −20°C to about 80°C an organic diisocyanate of the formula OCN—R'—NCO with a diamine of the formula R''—NH—R—NH—R'' such that the NCO/NH ratio is from 2.5 : 1 to 20 : 1.

* * * * *